United States Patent [19]

Carey

[11] Patent Number: 5,180,481
[45] Date of Patent: Jan. 19, 1993

[54] PHOSPHATE SELECTIVE COMPOSITION AND ELECTRODE

[76] Inventor: Clifton Carey, 116 Meem Ave., Gaithersburg, Md. 20877

[21] Appl. No.: 856,689

[22] Filed: Mar. 24, 1992

[51] Int. Cl.$^5$ ............................................. G01N 27/26
[52] U.S. Cl. .................................... 204/416; 204/435; 204/418
[58] Field of Search ......................... 204/416, 435, 418; 540/460, 474, 492, 575

[56] References Cited

U.S. PATENT DOCUMENTS

| | | | |
|---|---|---|---|
| 3,483,112 | 2/1968 | Ross | 204/416 |
| 4,174,428 | 11/1979 | Tabushi et al. | 525/334 |
| 4,900,818 | 2/1990 | Czech | 540/454 |

OTHER PUBLICATIONS

Potentiometric Adenosine Triphosphate Polyanion Sensor Using a Lipophilic Macrocyclic Polyamine Liquid Membrane, Umezawa, Kataoka and Takami, 1988, pp. 2392-2396.
A Study of New Bis(macrocyclic polyamine) Ligands as Inorganic and Organic Anion receptors, Kimura, Kuramoto, Koike, Fujioka and Kodama, 1989, pp. 42-46.
Distinctive Coordination Chemistry and Biological Relevance of Complexes with Macrocyclic Oxo Polyamines, Kimura, 1986, pp. 1-28.
Utilization of Chemical and Structural Characteristics of Tetraaza Cycloalkane Complexes, Ito, Kato, Yamashita and Ito, 1985, pp. 29-52.
Complexation of ATP to a Synthetic [15]$_3$—N$_3$ Macrocyclic Polyammonium Receptor, Narecek, Fischer and Burrows, 1988, pp. 6231-6234.
Anion-Receptor Molecules: Macrocyclic and Macrobicyclic Effects on Anion Binding by Polyammonium Receptor Molecules, Hosseini and Lehn, 1988, pp. 749-756.
The Complexation Equilibria of Mercury(II) Ions with Macromonocyclic 16-Membered Dioxopentamine, 18-Membered Dioxohexamine, and Their Related Compounds, Kodama and Kimura, 1989, pp. 3093-3097.
Binding of AMP, ADP, and ATP Nucleotides by Polyammonium Macrocycles, Hosseini and Lehn, 1987, pp. 1312-1319.
Developments in Functionalization of Macrocyclic Polyamines, Kimura, 1989, pp. 823-828.
Recent Advances in the Design of Anion-selective Membrane Electrodes, Chang, Kliza, Cha, Yim and Meyerhoff, 1990, pp. 10-21.

Primary Examiner—John Niebling
Assistant Examiner—Bruce F. Bell

[57] ABSTRACT

Phosphate ion-sensitive composition and ion-selective electrode are disclosed incorporating an ionophore having the formula:

$$R_1 - X \qquad (a)$$

or $$X - Z - X \qquad (b)$$

wherein $R_1$ is H or a hydrophobic substituent, Z is a spacing unit and X is represented by the formula:

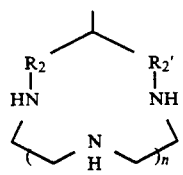

wherein n=0 or 1 and $R_2$ and $R'_2$ are independently selected from the group consisting of $CH_2$, $C(O)$ or $C(S)$.

6 Claims, 2 Drawing Sheets

□ Phosphate   △ Chloride
∗ Nitrate     ◇ Acetate
★ Sulfate     + Lactate

□ Phosphate   △ Chloride
* Nitrate     ◇ Acetate
☆ Sulfate     + Lactate

PHOSPHATE SELECTIVE COMPOSITION AND ELECTRODE

BACKGROUND OF THE INVENTION

1. Technical Field

This invention relates to the use of an anion selective compound in a membrane to measure the amount of a specific anion of choice in aqueous solution.

2. Background Art

Existing ion selective electrodes specific for anions typically have poor response characteristics including small linear ranges, high detection limits, and many interferences. Prior attempts to design such anion-specific electrodes have met with considerable difficulty. There is a need for a phosphate ion selective electrode having good selectivity and response characteristics employing existing electrode designs. With such a usable ion selective electrode, non-destructive techniques for the measurement of phosphate anions by an ion selective electrode can be applied to all areas of measurement science including environmental, medical and industrial applications.

Because phosphate anions are ubiquitous, an ion selective electrode selective for phosphate anions is particularly desirable. There have been numerous attempts to fabricate membranes suitable for such use. These attempts have included the formation of membranes from insoluble phosphate salts, and the incorporation of enzymes in the membrane to promote enzymatic reactions in the membrane. Unfortunately these systems have failed to yield anything but poorly responding electrodes with high detection limits or unsuitably high interferences from other common anions, thus rendering them of no practical use.

U.S. Pat. No. 3,857,777 to Guilbault et al, describes a phosphate selective electrode based on membranes containing a mixed complex consisting of silver, thiourea, and $HPO_4^{2-}$. Unfortunately, selective electrodes based on this system suffer from severe interferences such as $Cl^-$, $NO_3^-$, and other abundant anions. Furthermore this electrode deteriorates rapidly and does not produce consistent results after three days.

U.S. Pat. Nos. 4,735,692 and 4,900,404, to Arnold et al, describe a group of organo-tin compounds selective to $HPO_4^{2-}$ ions used to produce a membrane electrode selective to phosphate. These organo-tin compounds specifically bis(p-chlorobenzyl)tin dichloride are thought to complex phosphate anions preferentially. It was later determined that these electrodes suffer from severe interferences from other commonly occurring anions and that electrodes based on the bis(p-chlorobenzyl)tin dichloride are actually more sensitive to $SCN^-$ than phosphate. Additionally, electrodes based on these compounds have a linear range only to about $10^{-3}$ mol/l $HPO_4^{2-}$ thereby rendering them unsuitable for many applications.

Thus prior attempts at producing phosphate anion selective electrodes have been ineffective due to interferences from other anions and have exhibited poor sensitivity. Clearly there is a need for an effective and reliable phosphate ion selective membrane for use in ion selective electrodes.

SUMMARY OF THE INVENTION

The present invention describes a series of organic compounds that contain two or three nitrogen atoms in a N-heterocyclic structure. Each N-heterocyclic structure acts as a phosphate receptor and accommodates a dibasic phosphate anion ($HPO_4^{2-}$) by forming a complex or by adsorption. The phosphate receptor is incorporated into an appropriate solvent or support medium to fabricate an ion selective electrode that displays high selectivity and superior linear ranges. Measurements taken in aqueous solutions containing dibasic phosphate anions yield calibrated activity curves that are directly applicable to measure the $HPO_4^{2-}$ anion content in unknown samples.

The N-heterocyclic compounds of the present invention are highly selective for $HPO_4^{2-}$ anions. These ring structures also preferably have a pendant hydrophobic chain attached to the ring structure to enhance solubility into hydrophobic solvents, and carbonyl groups that may stabilize the entry of the $HPO_4^{2-}$ into the N-heterocyclic carrier complex. Electrodes made with membranes containing this compound are highly selective for $HPO_4^{2-}$ over $H_2PO_4^-$, $Cl^-$, $NO_3^-$, $SO_4^{2-}$, lactate, acetate, and $OH^-$ anions. These electrodes are superior to electrodes fabricated in the prior art as the present electrodes display both a superior limit of detection and linear range for the dibasic phosphate ion. The electrodes of the present invention have a limit of detection of 0.2 $\mu mol/l$ phosphate and a linear range from 1.0 $\mu mol/l$ to 100 mmol/l.

The principal object of the present invention is to provide membranes for use in electrochemically detecting the presence of dibasic phosphate ($HPO_4^{2-}$) anions.

Another object is to provide a phosphate selective electrode that has superior sensitivity.

Another object is to provide a phosphate selective electrode that has superior selectivity over other common anions.

Another object is to provide a phosphate anion selective electrode having continuing utility over a prolonged period of time.

Another object is to provide a phosphate selective electrode capably of performing $HPO_4^{2-}$ anion measurements that are not adversely affected at a pH between 6 and 8.

Another object is to provide a phosphate selective electrode that selectively monitors a dibasic phosphate ion content of an aqueous sample without interference from the remaining components in biological, industrial, or environmental samples.

Another object is to provide a method of using a dibasic phosphate anion selective electrode containing a N-heterocyclic compound for direct measurement of the dibasic phosphate anion activity (content) of a sample.

DESCRIPTION OF THE PREFERRED EMBODIMENT

Figure 1:
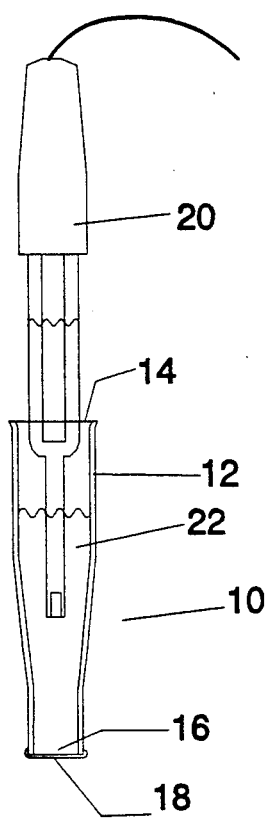
FIG. 1 displays a schematic representative of an anion selective electrode.

The present phosphate anion sensing compositions are N-heterocyclic compounds selected from the formulas:

$$R_1-X \quad (I)$$

or $$X-Z-X \quad (II)$$

wherein X is a heterocyclic ring of the formula:

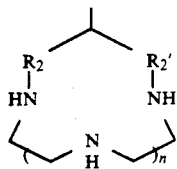

wherein n=0 or 1, $R_1$ is H or a hydrophobic substituent including substituted or unsubstituted alkyl group having 1 to 18 carbon atoms, $R_2$ and $R'_2$ are independently $CH_2$, $C(O)$ or $C(S)$ and Z is a spacing unit.

As defined in formula I, $R_1$ is H or a hydrophobic substituent, such as a substituted or unsubstituted $C_1$ to $C_{18}$ alkyl group, most preferably a $C_6$ to $C_{12}$ alkyl group. Suitable substituents on the substituted alkyl groups include but are not limited to alkoxy, alkylthio, aryl and aryloxy groups and the like.

The spacing unit Z between two N-heterocyclic rings is relatively uncritical as long as it does not contain reactive pendant groups that interfere with the synthesis of the N-heterocyclic rings during the preparation of the compounds of formula II. Typical examples of spacing units include but are not limited to:

$$-(CH_2)_m-, \quad -(CH_2)_m-O-(CH_2)_{m'}-,$$

wherein m and m' independently vary between 2 to 10, preferably 3 to 8.

The present invention utilizes a N-heterocyclic compound of formulas I or II as an ionophore or a phosphate receptor in an electrode sensor for sensing the dibasic phosphate anion ($HPO_4^{2-}$) concentration in an aqueous medium being tested. The sensor is preferably in the form of an ion sensitive electrode having a liquid or solid membrane containing the phosphate receptor, i.e., N-heterocyclic compound.

The ionophores of the present invention have two or three nitrogen atoms located within the heterocyclic ring structure varying the size of their cyclic structure. In a preferred embodiment of the present invention, 3-$C_{4-12}$ alkyl-1,5,8-triazacyclodecane-2,4-dione, preferably 3-decyl-1,5,8 triazacyclodecane-2,4-dione, (DTADD) the N-heterocyclic compound shown in Formula I in which n=1, $R_2$ and $R'_2$ are >C=O and $R_1$ is $C_{10}H_{21}$, is incorporated into a membrane to produce an ion selective electrode selective for dibasic phosphate ($HPO_4^{2-}$) that is superior to any reported in the literature in its selectivity and sensitivity characteristics. The partial negative charge of the carbonyl groups preferably attached to the ring serves to direct the dibasic phosphate anion to the center of the ring structure. However, these carbonyl groups are not necessarily required for this compound to function as a phosphate anion selective material, however it is believed that these groups serve to increase the selectivity. Any substituent H or hydrophobic $R_1$ sufficient to allow the N-heterocyclic compound to be solvated into a hydrophobic matrix can be employed. This hydrophobic substituent should have no effect on the anion complexing function of the N-heterocyclic compound.

A variety of ion sensitive electrodes each employing ion sensitive polymeric membrane are known in the art and are applicable for carrying out the method of phosphate concentration measurement according to the present invention. For example, electrodes wherein the membrane separates a solution to be tested from an internal reference solution are widely used. Such a membrane may comprise the ionophore, a hydrophobic binder or supporting matrix, e.g. poly(vinylchloride), and a compound capable of solvating the ionophore, e.g. a hydrophobic carrier solvent. A suitable liquid membrane contains the ionophore and a hydrophobic carrier solvent. The ionophore must be capable of sequentially complexing the desired ion, transporting the ion through the membrane and releasing the ion.

Electrochemical sensors formed from an electrode body having an ion sensitive polymeric membrane coated thereon are also well known. One such type of membrane electrode is commonly referred to as a coated wire electrode. Such an electrode may contain a molecular dispersion or a solution of an ionophore supported on a metal wire by a polymer matrix. The composition of this membrane may be identical to that of the membranes described above but the membrane does not have to meet the requirement of being self supporting. Typical coated wire electrodes are described in U.S. Pat. No. 4,115,209.

Another type of electrode having an ion sensitive membrane coated thereon relies on the effect of the electric field in the vicinity of the membrane. For example, U.S. Pat. No. 4,020,830 describes a chemical sensitive field effect transistor transducer capable of selectively detecting and measuring chemical properties of substances to which the transducer is exposed.

Binders for use in the ion selective membrane of the present invention include any of the hydrophobic natural or synthetic polymers capable of forming thin films of sufficient permeability to produce in combination with the ionophores and ionophore solvent(s) apparent ionic mobility across the membrane. Specifically, poly(vinylchloride), vinylidene chloride, acrylonitrile, polyurethanes (particularly aromatic polyurethanes), copolymers of poly(vinylchloride) and polyvinylidene chloride, polyvinyl butyral, polyvinyl formal, polyvinylacetate, silicone elastomers, and copolymers of polyvinyl alcohol, cellulose esters, polycarbonates, carboxylated polymers of polyvinyl chloride and mixtures and copolymers of such materials have been found useful. Films of such materials which include the ionophores and carrier solvents may be prepared using conventional film coating or casting techniques and may be formed either by coating and film formation directly over the internal reference electrode or some suitable interlayer or by formation separately and lamination thereto.

For certain electrodes, the membrane requires a carrier solvent. The carrier solvent provides ion mobility in the membrane and, although the ion transfer mechanism within such membrane is not completely understood, the presence of a carrier solvent is apparently necessary to obtain good ion transfer.

The carrier solvent must, of course, be compatible with the membrane binder and be a solvent for the carrier. The carrier solvent should also possess two other desirable characteristics: One characteristic is that the carrier solvent be sufficiently hydrophilic to permit rapid wetting of the membrane by an aqueous sample applied thereto to permit ionic mobility across the interface between the sample and the membrane. Alternatively, the carrier must be rendered hydrophilic by the action of a suitable non-interfering surfactant which improves contact between the samples in contact with the membrane and the carrier. The other highly desirable characteristic is that the carrier solvent be sufficiently insoluble in water that it does not migrate significantly into an aqueous sample contacted with the surface of the membrane as described hereinafter. Generally, an upper solubility limit in water would be about $10^{-3}$ mol/L. Within these limits, substantially any solvent for the ionophore which is also compatible with the binder may be used. As mentioned above, it is, of course, preferred that the solvent also be a plasticizer for the binder. It is also desirable that the ion carrier solvent be substantially non-volatile to provide extended shelf life for the electrode. Among the useful solvents are dibutyl sebacate, n-pentanol, isopentanol aromatic ethers and the like.

The ion selective membranes contain the described components over a wide range of concentrations. The membrane may contain the ionophore in an amount from 1 to 65 percent by weight, preferably, the ionophore is present in an amount from 20 to 50 percent by weight. In general, it is essential to employ the ionophore in the least amount necessary to provide the required response. Some membranes comprise a hydrophobic binder having the solvent and ionophore dispersed therein.

The carrier solvent is present in an amount sufficient to solvate the ionophore. The amount therefore depends on the particular solvent and ionophore chosen. More solvent may be used than is necessary to solvate the ionophore so that it remains solvated under a variety of storage conditions.

The amount of hydrophobic binder which is present is determined by the desired thickness of the membrane and by the necessity for providing support for the ionophore solvent dispersion. The thickness of the membrane will depend on the type of electrode in which it is used. For example, the preferred thickness of a liquid or a self supporting membrane used to separate two solutions may be in the range form 0.1 to 0.5 mm.

The ion selectivity of membrane electrodes can be observed by measuring the steady state difference in electrical potential between solution 1 and solution 2 (both usually aqueous) in the cell arrangement schematically represented by the following:

Ref. electrode 1/Solution 1//Membrane//Solution 2/Ref. electrode 2.

The calculations required to determine the ionic activity of solution 2 (generally the solution of unknown concentration) are derived from the well known Nernst Equation.

The electrode of the invention may incorporate an integral reference electrode. In this embodiment the electrode includes within its structure substantially all of the components needed for making a potentiometric determination with the exception of a second reference electrode, the potential indicating device and associated electrode so that in use the user merely needs to associated electrode so that in use the user merely needs to provide for contacting the sample with the ion selective membrane, e.g. by application of a small quantity of the sample to be analyzed (in the order of <50 μL) thereto and making the necessary electrical connections. Automated dispensers for applying controlled amounts of sample to the electrode at the appropriate location are known and any such dispenser, or for that matter careful manual dispensing, may be used to contact the sample with the electrode. Alternative, the electrode may actually be immersed in or contacted with the surface of the solution under analysis.

Reference electrodes such as silver/silver chloride and saturated calomel electrodes for use in combination with the electrodes of the present invention are also well known.

Similarly, potentiometers capable of reading the potentials generated in the ion selective electrodes of the present invention are well known and can be used to give an indication of the potential from which the ionic activity in the unknown solution may be calculated. By incorporating computing capability into the potentiometric device it is, of course, possible to obtain direct readings of specific ionic concentrations in solution as a function of ionic activity.

Referring to the drawings, FIG. 1 shows a typical ion selective electrode 10 having an outer sleeve 12 with an upper opening 14 and a lower opening 16 sealed with an anion selective membrane 18. An internal reference electrode 20 is positioned through the upper opening 14 and extending into an internal fill solution 22 contained within the electrode 10. The membrane 18 owes its sensitivity for dibasic phosphate anions to a N-heterocyclic compound of the present invention functioning as a phosphate receptor or ionophore.

These N-heterocyclic compounds are easily incorporated into a variety of electrode types such as the coated wire, liquid ion exchanger, pressed pellet, and selective membrane structures. One variety of ion selective electrode structure includes the N-heterocyclic compound together with dibutyl sebacate (Eastman Kodak Co., Rochester, N.Y.) as a plasticizer in a poly(vinylchloride) (PVC) (Aldrich Chemical Co., Inc. Milwaukee, Wis.) matrix. These anion selective electrodes are constructed by formation of a PVC matrix membrane over the open end of an electrode body by dipping the electrode body into a mixture containing PVC (45% w/w), the N-heterocyclic compound (20% w/w), and dibutyl sebacate (35% w/w) mixed with enough tetrahydrofuran (THF) to dissolve the PVC. The dipped electrode body together with the liquified membrane is allowed to air dry 24 hours.

The following examples are given to illustrate the present invention in detail, but the embodiments of the present invention are not limited by these examples.

EXAMPLE 1

(1) Synthesis of ethyl n-decylmalonate precursor

A one liter round bottomed flask with a stir bar and a reflux condenser attached was charged with 373 ml of 2.68 mol/L sodium ethoxide (one mole) and 127 ml absolute ethanol. To this mixture, while in a water bath at 45° C., 176.19 g (167 ml) of diethyl malonate (1.1 mol) was slowly added over the period of 30 min. One mol (221.19 g, 207 ml) of n-decylbromide was added slowly to this mixture over the period of 30 min. The color of the solution went from a clear brown-orange to an opaque yellow color. The mixture was refluxed for two hours and the ethanol solvent was then removed by distillation. The mixture was cooled to room temperature and was transferred to a separatory funnel and extracted into 550 ml of $H_2O$. The resultant two layers were of the same brown color with the top layer containing the product. This top layer was collected and vacuum distilled to remove the remaining ethanol. A clear slightly straw colored liquid was obtained weighing 280.86 g representing a 93.5% conversion and having a boiling point of 140°–145° C. under 700 mm Hg vacuum.

(2) Synthesis of 3-decyl-1,5,8-triazcyclodecane-2,4-dione (DTADD)

A one liter round bottomed flask was charged with 0.076 mol (22.80 g) of ethyl α-decylmalonate (from above), 0.076 mol (7.74 g) diethylene triamine and 500 ml absolute ethanol. The mixture was refluxed for 42 days. During this period two ml aliquotes of solution were removed by hypodermic syringe on days 7, 15, 22, and 37 for NMR analysis to determine the completeness of the reaction. After termination of the reflux, the ethanol was removed under reduced pressure and the product recrystallized from cold acetonitrile to yield 14.71 grams of a white heavy precipitate representing approximately a 62.1% conversion and having NMR characterizations in $CDCL_3$, with signals reported in ppm downfield relative to TMS:

$^1$H-NMR Quartet 3.7, $CH_2-CH_2-NH-C=O$, 4 H; Multiplet 3.3, $CH_3-(CH_2)_8-C\overline{H_2}-CH-$, 1 H; Multiplet 2.8, $CH_2-NH-CH_2$, 4 H; Broad Singlet 1.8, $CH_3-(CH_2)_8-CH_2-CH-$ & NH, 5 H; Multiplet, 1.3, $CH_3-(CH_2)_8-C\overline{H_2}-$, 16 H; Triplet, 0.9, $C\underline{H_3}-(CH_2)_8-CH_2-$, 3 H.

(3) Synthesis of 3-decyl-1,5-diazacyclo-heptane-2,4-dione

The titled compound is prepared by utilizing the procedure of Example 1 synthesis (2) and substituting ethylenediamine (1,2-diaminoethane) in a molar equivalent for diethylene triamine.

(4) Synthesis of 3-decyl-1, 5, 8, 11-tetrazacyclotridecane-2,4-dione for comparative example.

A one liter round bottomed flask was charged with 0.053 mol (15.9 g) of ethyl n-decylmalonate, 0.053 mol (7.738 g) triethylene tetramine, and 500 ml absolute ethanol. During refluxing for 42 days, 2 ml aloquotes were removed by hypodermic syringe on days 7, 15, 22, and 37 for NMR analysis to determine the completeness of the reaction. After termination of the reflux the ethanol was distilled away and the product recrystallized from cold acetonitrile to yield 10.89 g of a very light fluffy white precipitate representing approximately a 60.0% conversion to the titled compound.

EXAMPLE 2

Synthesis of 3-decyl-1,5,8-triazacyclodecane

The cyclic diamide (5 millimoles) obtained in Example 1, syntheses (2) is added little by little while cooling to 30 milliliters of a solution of diborane (18 milli moles) in tetrahydrofuran, allowed to stand for 30 minutes and then heated for 5 hours to distill away the tetrahydrofuran. To the residue is added 20 ml of 6N HCl. The mixture was heated for three hours and the solvent is distilled away under reduced pressure. The residue is dissolved in a mixed solvent of ethanol-water (5:1) by heating. On cooling the solution obtained above, the hydrochloric acid salt precipitates.

About 400 ml of an anion exchange resin (Amberlite IRA-400) which is washed with aqueous solution of sodium hydroxide and water is charged to a column. The above hydrochloric acid salt dissolved in about 150 ml of water is flowed through the above column, and further about 500 ml of water is flowed down through the column. The water is distilled away from the effluent to obtain crystals of the titled compound.

EXAMPLE 3

Synthesis of 1,3-bis(1,5,8-triazacyclodecane-2,4-dione)propane

A mixture of 45 mmol. of 2,2'-(1,3-propanediyl)-bis(-diethyl malonate) and 81 mmol. of diethylene triamine in 0.7 liters of dry methanol is refluxed for three weeks. After evaporation of the solvent, $CH_3CN$ is added to crystallize the residue. Recrystallization from $MeOH/CH_3CN$ yields the titled compound.

EXAMPLE 4

Synthesis of 1,3-bis(1,5,8-triazacyclodecane)-propane

The product of Example 3 is reduced with freshly distilled $BH_3THF$ (77 mmoles) in 200 ml of THF to yield the titled compound.

EXAMPLE 5

Dibasic Phosphate Anion Determination

An electrode of the structure shown in FIG. 1 was produced containing a membrane containing PVC (45% w/w), the DTADD ionophore (20% w/w), and dibutyl sebacate (35% w/w). The phosphate-selective electrode that contained the DTADD N-heterocyclic ionophore was soaked in a 0.2 mol/ $K_2PO_4$ solution at pH 7.2 for 24 hours before use.

Figure 2:
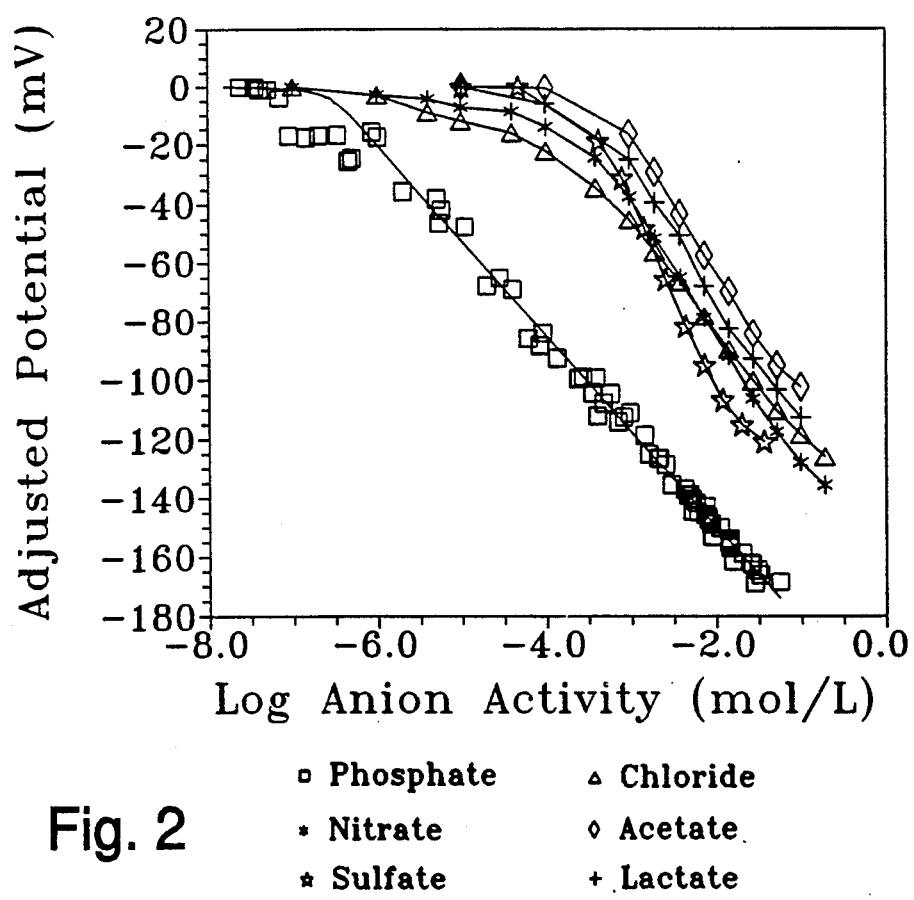
FIG. 2 displays the response characteristics of the phosphate electrode of the present invention to the activity of dibasic phosphate and various other anions in aqueous solution at pH 7.2.
Figure 3:
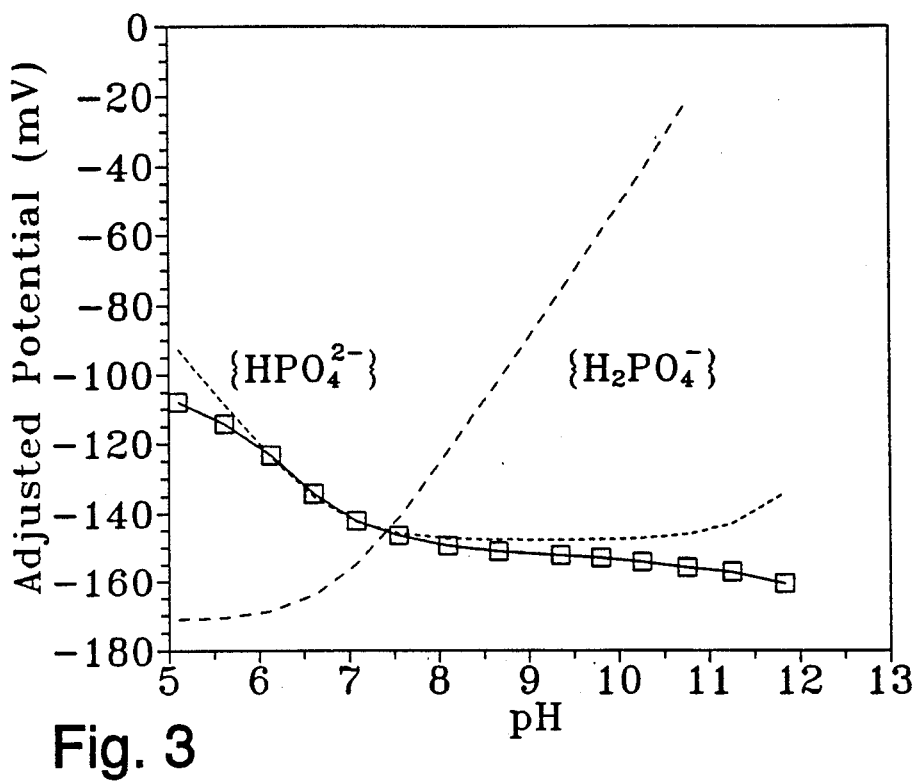
FIG. 3 displays the response characteristics of the phosphate electrode of the present invention to the activity of dibasic phosphate anions as a function of pH as shown by solid curve.

FIG. 2 shows the response characteristics of the anion selective electrode utilizing a PVC membrane as prepared above containing 3-decyl-1,5,8-triazacyclodecane-2,4-dione (DTADD) to the activity of various anions including dibasic phosphate, chloride, sulfate, nitrate, lactate, and acetate in aqueous solutions at pH 7.2. The response of this electrode to changes in the pH at a constant total phosphate concentration of 50 mmol/L is shown in FIG. 3. The broken curves of FIG. 3 represent the predicted electrode response as a function of pH for $H_2PO_4^-$ and $HPO_4^{2-}$ species and the solid curve is the actual response of the electrode.

The response characteristics were determined following standard addition procedures at pH 7.2. The effect of pH on the function of the electrode was determined by changing the pH of a 50 mmol/L phosphate solution by adding small aliquots of concentrated acid ($HNO_3^-$) or base (KOH) such that the pH varied between 5 and 12. The phosphate electrode had a slope of 29 mV/conc. decade, and a linear range from 1.0 µmol/L to 100 mmol/L (FIG. 2). As can be seen in FIG. 3 performance of the electrode of the present invention was not adversely affected by pH between pH 6 and 8 and it displayed FIG. 2 demonstrates the good selectivity of dibasic phosphate anions over common anions such as acetate, lactate, chloride, sulfate, and nitrate.

The selectivity of the phosphate selective electrode over other anions was quantified using the single solution $K_{i,j}$ method The activity ratios of $HPO_4^{2-}$ over the other anions near the midpoint of the linear range (0.3 mmol/L) are as follows: K(HPO$_4$,Cl) 0.0045, K(HPO$_4$,NO$_3$) 0.0017, K(HPO$_4$,SO$_4$) 0.001, K(HPO$_4$,Lac) 0.001, and K(HPO$_4$,Ace) 0.0006. Values less than one (1) indicate that the electrode is selective to HPO$_4^{2-}$ than the interfering anion. The smaller the value the greater the selectivity of the electrode. Values greater than one (1) indicate that the electrode is more selective to the interfering anion than HPO$_4^{2-}$. Thus the selectivity pattern for this electrode is: HPO$_4^{2-}$>>Cl$^-$>NO$_3^-$>SO$_4^{2-}$=Lac>>Ace$^-$. Further, FIG. 3 clearly shows that the electrode responds to the dibasic phosphate species (HPO$_4^{2-}$) and not the monobasic phosphate species (H$_2$PO$_4^-$). The K(HPO$_4$,H$_2$PO$_4$) values depend on the pH of the measurement and does accurately reflect the ability of the electrode to distinguish between these two species. Experiments have shown that the phosphate-selective electrode does not deteriorate for a period of over 8 months. The use of the electrode over this period of time included quantifying the phosphate activity in untreated human saliva, complex saturated calcium-phosphate solutions, and in numerous mixed standards. Based on the superior selectivity and sensitivity of this phosphate selective electrode, its robust nature, and long lifetime, application to a wide variety of measurement systems is possible.

EXAMPLE 6 (Comparative)

Figure 4:
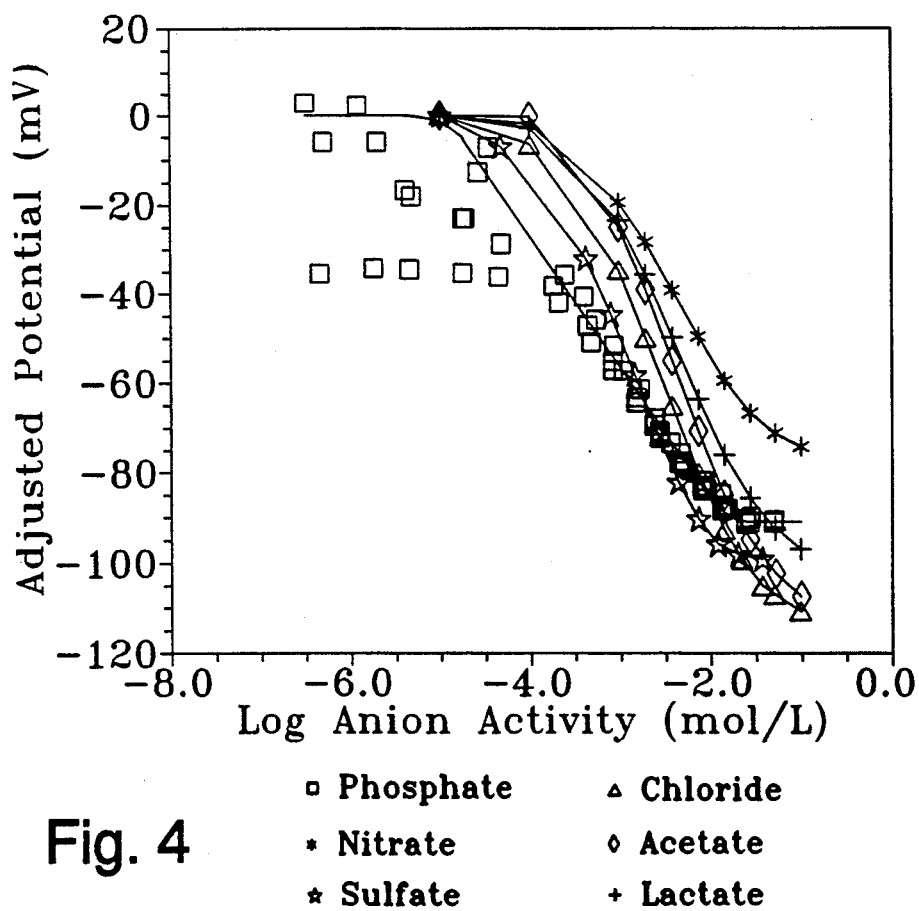
FIG. 4 displays the response characteristics of a comparative phosphate electrode.

Dibasic Phosphate Anion Determination Using 3-decyl-1,5,8,11-tetrazacyclotridecane-2,4-dione In accordance with the procedure of Example 5, an electrode was produced substituting 3-decyl-1,5,8,11-tetrazacyclotridecane-2,4-dione for DTADD. The response characteristics of this electrode as to selectivity to various common ions is displayed in FIG. 4. This electrode displays inferior sensitivity and selectivity in comparison to the electrode of Example 5 containing DTADD.

Table I displays the response characteristics and Table II displays the selectivity characteristics of the membrane of the present invention of Example 5 containing DTADD versus the membrane prepared in comparative Example 6.

TABLE I

| | Slope {HPO$_4^{2-}$} mV/decade | Linear Range mol/L to mol/L | | Useable pH Range |
|---|---|---|---|---|
| | | Lower | Upper | |
| Example 5 | −28.9 | 1 × 10$^{-3}$ | 1 × 10$^{-1}$ | 6 to 8 |
| Example 6 | −24.3 | 2 × 10$^{-5}$ | 9 × 10$^{-3}$ | 6 to 9 |

TABLE II

| | K$_{ij}^{Pot}$ Selectivity Coefficient Relative to HPO$_4^{2-}$ | | | | |
|---|---|---|---|---|---|
| | Cl$^-$ | NO$_3^-$ | SO$_4^{2-}$ | Lac$^-$ | Ace$^-$ |
| Example 5 | 0.0045 | 0.0017 | 0.001 | 0.001 | 0.0006 |
| Example 6 | 0.14 | 0.05 | 0.27 | 0.06 | 0.06 |

While the description of and some examples contained in this invention have been disclosed, some additional modifications such as variations in the N-heteocyclic structure, quantity of ion exchanger in the membrane, and structure of the ion selective electrode may occur to those skilled in the art; therefore it is intended herein to cover all such modifications that fall within the true spirit and scope of this invention.

What is claimed is:

1. A dibasic phosphate ion selective membrane electrode comprising:
    a) a conductive body member having an opening therein,
    b) a membrane covering the opening comprising an ionophore represented by the following formulas:

$$R_1-X- \quad (1)$$

or

$$X-Z-X \quad (2)$$

wherein R$_1$ is H or a hydrophobic substituent, Z is a spacing unit and X is represented by the formula:

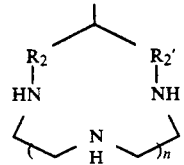

wherein n=0 or 1 and R$_2$ and R'$_2$ are independently selected from the group consisting of CH$_2$, C(O) or C(S),
    c) a reference solution contained within said body member, and
    d) a reference electrode disposed with said body member in contact with the reference solution.

2. The membrane electrode as defined in claim 1 wherein the membrane is a liquid membrane comprising the ionophore and a hydrophobic carrier solvent.

3. The membrane electrode as defined in claim 1 wherein the membrane comprises the ionophore in a supporting matrix.

4. A dibasic phosphate ion sensitive electrode having an ion-sensitive membrane comprising:
    a) an ionophore having the formula:

$$R_1-X \quad (1)$$

$$X-Z-X \quad (2)$$

wherein R$_1$ is H or a hydrophobic substituent, Z is a spacing unit and X is represented by the formula:

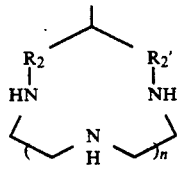

wherein n=0 or 1 and R$_2$ and R'$_2$ are independently selected from the group consisting of CH$_2$, C(O) or C(S).

5. The electrode as defined in claim 4 wherein the membrane comprises the ionophore in a supporting matrix.

6. The electrode of claim 4 wherein R$_1$ is substituted or unsubstituted alkyl or substituted or unsubstituted aryl.

* * * * *